(12) United States Patent
Luotola et al.

(10) Patent No.: US 7,709,212 B2
(45) Date of Patent: May 4, 2010

(54) PARTICLE BASED BINDING ASSAY

(75) Inventors: Juhani Luotola, Espoo (FI); Hannu Nikula, Espoo (FI); Mira Murtovuori, Espoo (FI)

(73) Assignee: Orion Diagnostica Oy, Espoo (FI)

( * ) Notice: Subject to any disclaimer, the term of this patent is extended or adjusted under 35 U.S.C. 154(b) by 39 days.

(21) Appl. No.: 11/720,701

(22) PCT Filed: Nov. 23, 2005

(86) PCT No.: PCT/EP2005/012523

§ 371 (c)(1),
(2), (4) Date: Jul. 25, 2007

(87) PCT Pub. No.: WO2006/058645

PCT Pub. Date: Jun. 8, 2006

(65) Prior Publication Data

US 2008/0160537 A1    Jul. 3, 2008

(30) Foreign Application Priority Data

Dec. 3, 2004    (GB) ................................. 0426592.2

(51) Int. Cl.
*G01N 33/53* (2006.01)
(52) U.S. Cl. ........................... 435/7.1; 435/6; 435/7.92; 435/7.93; 435/7.94; 435/288.6; 435/971; 435/975; 436/514; 436/518; 436/539; 436/824; 436/524; 436/525
(58) Field of Classification Search .............. 435/6, 435/7.1, 7.92, 7.93, 7.94, 288.6, 971, 975; 436/514, 518, 539, 824, 524, 525
See application file for complete search history.

(56) References Cited

U.S. PATENT DOCUMENTS 4,054,646 A    10/1977    Giaever (Continued)

FOREIGN PATENT DOCUMENTS

EP    B-0253579 B1    3/1990

(Continued)

OTHER PUBLICATIONS

Härmä et al., "Zeptomole Detection Sensitivity of Prostate-Specific Antigen in a Rapid Microtitre Plate Assay Using Time-Resolved Fluorescence," Luminescence 15:351-355, 2000.

(Continued)

*Primary Examiner*—Bao-Thuy L Nguyen
(74) *Attorney, Agent, or Firm*—Clark & Elbing LLP

(57) ABSTRACT

The present invention provides a method for detecting the presence or amount of an analyte in a sample, said method comprising: a porous surface to which particles having attached thereto a binding substance, analyte and binding substance coated label particles are added. If said analyte is present in the sample an immuno- or chemical reaction occurs in the liquid phase. The separation of bound complex from unbound material is achieved by using said surface where the separation occurs mainly two dimensionally on the surface of the porous surface (e.g. grid). Interestingly, the disclosed surface enables a separation where said complexes are distributed two dimensionally on the porous surface (e.g. grid), whereas unbound materials are distributed three dimensionally. Accordingly, said surface enables both a two and a three dimensional separation.

23 Claims, 3 Drawing Sheets

U.S. PATENT DOCUMENTS

| | | | |
|---|---|---|---|
| 4,072,576 | A | 2/1978 | Arwin et al. |
| 4,219,335 | A | 8/1980 | Ebersole |
| 4,233,144 | A | 11/1980 | Pace et al. |
| 4,238,757 | A | 12/1980 | Schenck |
| 4,279,617 | A | 7/1981 | Masson et al. |
| 4,287,300 | A | 9/1981 | Gibbons et al. |
| 4,632,901 | A | 12/1986 | Valkirs et al. |
| 4,727,019 | A | 2/1988 | Valkirs et al. |
| 4,853,335 | A | 8/1989 | Olsen et al. |
| 4,859,612 | A * | 8/1989 | Cole et al. ............... 436/523 |
| 4,916,056 | A | 4/1990 | Brown et al. |
| 5,008,080 | A | 4/1991 | Brown et al. |
| 5,141,850 | A * | 8/1992 | Cole et al. ............... 436/525 |
| 5,149,622 | A | 9/1992 | Brown et al. |
| 5,236,826 | A | 8/1993 | Marshall |
| 5,284,748 | A | 2/1994 | Mroczkowski et al. |
| 5,501,949 | A | 3/1996 | Marshall |
| 5,565,366 | A | 10/1996 | Akers |
| 5,585,241 | A * | 12/1996 | Lindmo ............... 435/6 |
| 6,096,563 | A | 8/2000 | Hajizadeh et al. |
| 6,268,222 | B1 | 7/2001 | Chandler et al. |
| 6,632,603 | B1 * | 10/2003 | Hubscher et al. ............... 435/6 |
| 2002/0164670 | A1 | 11/2002 | Forrest |
| 2005/0214737 | A1 * | 9/2005 | Dejneka et al. ............... 435/4 |

FOREIGN PATENT DOCUMENTS

| | | |
|---|---|---|
| EP | B-0389003 B1 | 12/1992 |
| EP | B-0180638 B1 | 1/1993 |
| GB | 2123146 A | 1/1984 |
| WO | WO 91/13353 | 9/1991 |
| WO | WO 94/18565 | 8/1994 |
| WO | WO 97/31259 A1 | 8/1997 |

OTHER PUBLICATIONS

Härmä et al., "Europium Nanoparticles and Time-Resolved Fluorescence for Ultrasensitive Detection of Prostate-Specific Antigen," Clinical Chemistry 47(3):561-568, 2001.

International Search Report and Written Opinion from International Application No. PCT/EP2005/012523, dated Jun. 14, 2007.

Translation of Notice of Reasons for Rejection related to Japanese Patent Application No. 2007-543736, dated Dec. 19, 2008 (drafting date) and Dec. 22, 2008 (dispatch date).

Translation of Decision of Rejection related to Japanese Patent Application No. 2007-543736, dated Jun. 30, 2009 (drafting date) and Jul. 6, 2009 (dispatch date).

* cited by examiner

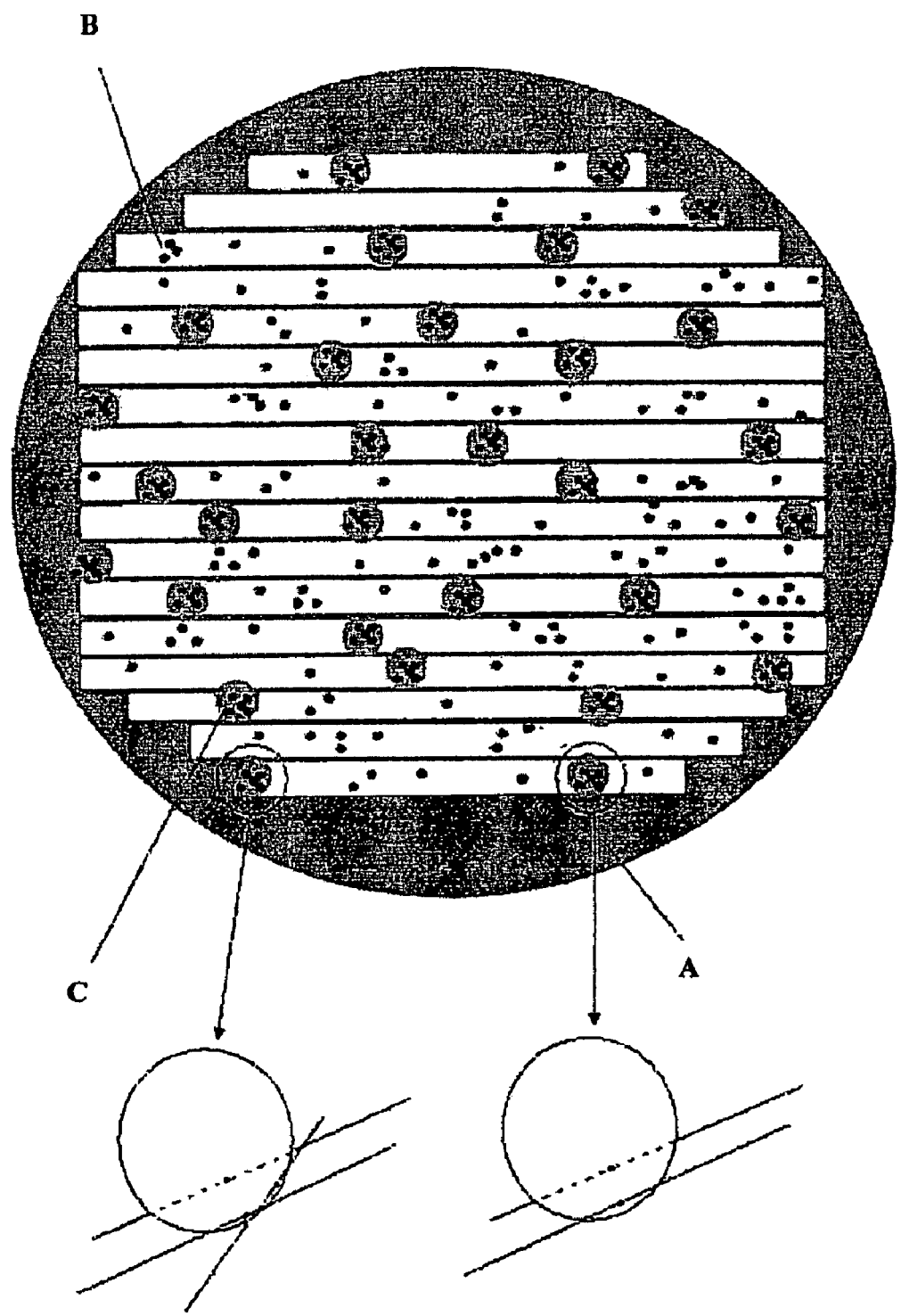
Figure 6   • = D

PARTICLE BASED BINDING ASSAY

CROSS-REFERENCE TO RELATED APPLICATIONS

This application claims priority under 35 U.S.C. §371 from international application PCT/EP2005/012523, filed Nov. 23, 2005, which claims priority from Great Britain Application No. 0426592.2, filed Dec. 3, 2004.

FIELD OF THE INVENTION

The present invention relates to separation of formed immunocomplex or any biomolecular complex from unbound material on a porous surface (e.g. grid) comprising holes/openings mutually compatible with used particles. The invention discloses a heterogeneous immunoassay performed in two-particle assay format where the size and different characteristics of the particles are exploited, for detection and quantification of an analyte in a sample. In the method, large particles are used to catch analyte from a sample, separate and distinguish said analyte from body fluids, whereas small particles are used as labelling means.

BACKGROUND OF THE INVENTION

Several methods use immunoassay techniques for detection and quantification of antigen in a specimen. Two types of immunoassay systems are currently used. In a homogeneous system, the assay is performed in a single phase. In a heterogeneous system, the immunoassay is performed in two steps. The additional step is needed to separate bound material from unbound. Typically, a solid support surface is used as a bound phase, to which antibody or antigen is attached via adsorption or chemical bonding. Many kinds of solid support surfaces have been developed to improve the performance of an immunological reaction and the efficacy of the separation step.

Particles have been used as a mobile solid phase in agglutination assays to improve the efficiency of the immunological reaction between antibody and antigen. In said system, soluble antigens/antibodies will combine with specific antibodies/antigens bound onto the particles resulting in precipitates of insoluble antigen-antibody immunocomplexes on the surface of the particles. In solid phase immunoassays, the sensitivity of the assay can be increased by washing the solid phase bound immunocomplex, which results in more complete separation of unbound material and thus in increase of signal to noise ratio. Additionally, microparticles of various compositions have also been used in an effort to increase the surface area of the solid support.

Particle based agglutination assays are well-known for those skilled in the art. The original agglutination assays exploited single sized particles as polystyrene particles i.e. latex particles. A method to overcome the low sensitivity of the agglutination assay especially when assaying small quantities of an analyte is disclosed in U.S. Pat. No. 4,279,617, where two different coated particulate reagents are used. Said particles may be of different size. Said method does not involve a separation of unbound material from the agglutinate using a filtration process.

Prior art documents acknowledge a number of publications disclosing assay techniques which rely on the use of a porous member such as a membrane, filter or other matrices. U.S. Pat. No. 4,632,901, EP-B-180638 and U.S. Pat. No. 4,727,019 disclose a member to which is bound a receptor for the target analyte and a second member to draw liquid added to the first member. When a liquid sample is added, the liquid flows through and the receptors in the member bind the analyte present in the sample. After the addition of the sample, another receptor for the analyte which is labelled is added to permit detection. Suitable labels being an enzyme, radionuclide or fluorescent label. When an enzyme label is used a disadvantage is that a colouring forming substrate must be added to the membrane.

EP-B-253579 discloses a further embodiment of the above mentioned member-based technique. The embodiment takes advantage of microspheres which are entrapped within the interstices of the porous membrane in order to embrace a means for fixing receptor or anti-receptor to the porous member.

U.S. Pat. No. 4,916,056, EP-B-389003, U.S. Pat. No. 5,008,080 and U.S. Pat. No. 5,149,622 disclose membrane based flow through assays exploiting particles onto which antibodies or antigens have been retentioned. The size of the particles is not critical although it is preferred that the size is smaller than the average pore size of the fibrous matrix.

Three dimensional membranes are commonly used for separation of immunocomplex from unbound material. U.S. Pat. No. 5,501,949 discloses an immunoassay using finely divided particles as a solid phase for the first binding component (substance). The soluble, second binding components are labelled with a signal generating material. The soluble, non-particle bound, labelled binding component used in this method has lower specific activity compared to binding component labelled with a particle bound label. This results in the loss of sensitivity of the assay. The method uses a three dimensional membrane for filtering the immunocomplex and separating the unbound material.

U.S. Pat. No. 4,853,335 discloses an immunoassay where a biological specimen, colloidal gold labelled ligand or anti-ligand, and solid phase capture particles coated with ligand or anti-ligand are applied on a porous film. The particles captured on the membrane are visually inspected for colour.

GB Application No. 2123146 describes an assay method accomplished in a dual channel optical-electrical cell counter or in a fluorescence microscope. The disclosure involves first and second microscopic particles having different detectable properties by performing said assay methods. Said application does not disclose any separation of unbound material from agglutinate using a filtration process. A biological fluid is intermixed with particles, whereafter their different properties are measured.

U.S. Pat. No. 5,565,366 comprises a method where a test mixture is formed by contacting a sample with coloured particles which bear on their surface receptors specific for the ligand. When the test mixture is passed through a filter having apertures larger than the particles but smaller than the aggregates, the aggregates are removed from the filtrate and the colour of the filter/filtrate is analysed. The document discloses that the used small particle size is more advantageous with regard to aggregate formation than larger particles used in prior art techniques. However, the use of small particles is disadvantageous since the consumption of ligand or anti-ligand on the particle is higher the smaller the particles are.

U.S. Pat. No. 6,268,222 discloses a different approach where microparticles are attached to nanoparticles labelled with fluorescence dye. The particles are attached to each other by their surface functional groups. This invention comprises a core or carrier particle having on its surface a plurality of smaller polymeric particles. When different fluorescence dyes are used, multiple fluorescence emission is obtained by a light source excitation. By varying the quantity and ratio of different populations of nanospheres, it is possible to establish and distinguish a large number of discrete populations of carrier particles with unique emission spectra. This approach is useful for multiplex analysis of a plurality of analytes in a sample.

As disclosed in the above review of prior art, particles alone or together with different applications of three dimensional membranes have been used to separate desired analytes from a sample. However, there is often unspecific binding of labelled binding substance due to the porosity of the membrane. Thus, the signal to noise ratio is low, due to a high background signal, when using three dimensional membranes. Hence, three dimensional membranes require considerable washing to reduce unspecific binding.

In addition to the methods disclosed above, assays exploiting, for example, magnetic beads are also well known for those skilled in the art.

The methods disclosed in the above prior art documents rely mainly on visual detection of analyte and are, therefore, not sensitive enough to measure low concentrations of analyte. Moreover, the level of signal created by the label is not, in all circumstances, intensive enough.

More sophisticated methods in the art apply the change in electrical current to indicate presence of analyte in sample. Field effect transistors coated with a layer of antibody in the gate region are utilised, for example, in U.S. Pat. No. 4,238,757 to detect antigen-antibody reaction by a change of charge concentration of the transition.

A tagged reagent which reacts with the analyte-reagent complex or with the reagent to change the electrical reactance of the surface is added in U.S. Pat. No. 4,219,335.

An immunologic reaction can also be measured by a voltameric immunoassay as disclosed in U.S. Pat. No. 4,233,144, where one immunoreactant is labelled with an electroactive substance.

U.S. Pat. No. 4,054,646 discloses a method where an antigen-antibody layer is sandwiched between two conducting layers and where the electric capacitance of the resulting laminate is measured.

Another type of capacitance-measuring technique which exploits a pair of electrodes coated with a substrate and immersed in a medium containing a material which specifically binds with the substrates is disclosed in U.S. Pat. No. 4,072,576.

It is also possible to combine a change effect signal detection with an enzyme immunoassay technique as described in U.S. Pat. No. 4,287,300.

However, the above electrical methods did not meet the needs of a simple, fast, sensitive, inexpensive and easy-to-use method to perform an immunodiagnostic assay.

A method intended to solve the above mentioned disadvantages is disclosed in U.S. Pat. No. 5,284,748 where antigen or antibody-labelled colloidal gold particles are employed optionally with silver enhancement in a new immunodiagnostic method. The complex so formed causes full or partial completion (closing) of an essentially open electrical circuit. A further embodiment comprises a pair of spaced-apart electrical conductors, particularly conductive layers disposed on a substantially non-electrically conductive base. There is a space between the conductors defined as a path or channel. Means forming an electrical circuit is contacted to each of the conductors so that the channel constitutes a break in the circuit. The binding reaction between the pair of substances is responsible for fully or partly bridging the break in the circuit. One such means involves adhering one of the substances to the surfaces of electrically conductive particles.

SUMMARY OF THE INVENTION

The present invention concerns a method for detecting the presence or amount of an analyte in a sample. The invention employs mobile capture particles coated with a first binding substance (i.e. first binding component) and detectably labelled particles coated with a second binding substance (i.e. second binding component). Both binding substances are a specific ligand or anti-ligand onto which the analyte (ligand or anti-ligand) molecule binds if present in the sample.

The present invention exploits said particles and relies on the use of a porous surface, i.e. separation means. Distinct from the prior art, the present invention takes advantage of the use of capture particles onto which a binding substance specific for the analyte in the sample has been bound. The produced complex will retain on the porous surface when applied thereon. Accordingly, the complex which consists of first binding component-analyte-second binding component or first binding component-analyte is separated from unbound material on the surface of the separation means. Consequently, this procedure can also be used for separation and enrichment of the analyte. Said enriched analyte can then be used for further procedures and studies.

Said porous surface may form the basic part of a device which additionally may comprise a frame, holder or other support forming, for example, an assay casing (cartridge).

For generation of an enhanced liquid flow for removing unbound material a wicking membrane and/or a negative or positive pressure or an external force (e.g. ultrasound) can be used.

The present invention exploits two and three dimensional separation means for segregation of the formed immuno/biomolecular complexes from unbound material after immuno- or chemical reactions. In such separation means, the immuno/biomolecular complex segregation occurs on the surface of the separation means. Interestingly, the disclosed porous surface enables a separation of said complexes two dimensionally on the surface whereas small label particles and other unbound materials by penetrating the surface are distributed three dimensionally. Consequently, both a two and a three dimensional separation is possible by using said porous surface. Therefore, if necessary, it is possible to release the produced immunoibiomolecular complexes from the surface and transfer them according to additional needs. The analyte itself or some other cellular component can be further characterised e.g. by PCR or by any other biochemical or molecular biology method being well known for those skilled in the art.

The present invention overcomes the sensitivity deficiencies of prior art methods by exploiting unlabelled and labelled particles of different size and a porous surface. A common problem with the label used in prior art methods is that it has an inappropriate signal intensity and signal to noise ratio. The size of the capture particles in relation to label particles in the present invention is optimised to consume a smaller but still optimal amount of ligand or anti-ligand when compared to small particles. According to the present invention, high background label counts, due to the high unspecific label binding, can be decreased by using a porous surface, which possess low unspecific label binding, for the separation of the immunocomplex from the unbound material. Moreover, the sensitivity of the assay can be increased by using a binding substance affixed to label particles, thus increasing the specific activity of the labelled binding substance and the assay sensitivity.

In particular, the present invention provides a method for detecting the presence or amount of an analyte in a sample, said method comprising: (a) applying to a porous surface a first binding component comprising particles having attached thereto a binding substance that specifically binds to said analyte; (b) applying said sample to said porous surface; (c) applying to said porous surface a second binding component comprising detectably labelled particles; and (d) detecting a signal produced by said detectably labelled particles on said porous surface which is indicative of the presence and/or amount of said analyte in said sample; wherein said porous surface allows said second binding component but not said first binding component to pass through said surface; wherein said first binding component and said analyte bind to each other to form a first binding complex; wherein said detectably labelled particles have attached thereto a binding substance that specifically binds to said first binding complex, such that said second binding component and said first binding complex bind to each other to form a second binding complex; and wherein the first binding complex and/or the second binding complex is retained on the porous surface. In one embodiment, the sample and first binding component are contacted with one another before being applied to the surface. In another embodiment, step (a) is carried out before step (b). In a further embodiment, the sample, first binding component and second binding component are contacted with one another before being applied to the surface. In a further additional embodiment, step (b) is carried out before step (a).

The invention also provides a kit for detecting the presence and/or amount of an analyte in a sample comprising:
  (a) a porous surface;
  (b) a first binding component comprising particles having attached thereto a binding substance that specifically binds to said analyte to form a first binding complex; and
  (c) a second binding component comprising detectably labelled particles which have attached thereto a binding substance that specifically binds to said first binding complex, such that said second binding component and said first binding complex bind to each other to form a second binding complex;
  wherein the first binding complex and/or the second binding complex are capable of being retained on the porous surface.

BRIEF DESCRIPTION OF THE DRAWINGS

FIG. 6 shows the separation of unbound second binding component (B) from second binding component bound to first binding component (C) using a grill structure (A).

DETAILED DESCRIPTION OF THE DRAWINGS

Figure 1:
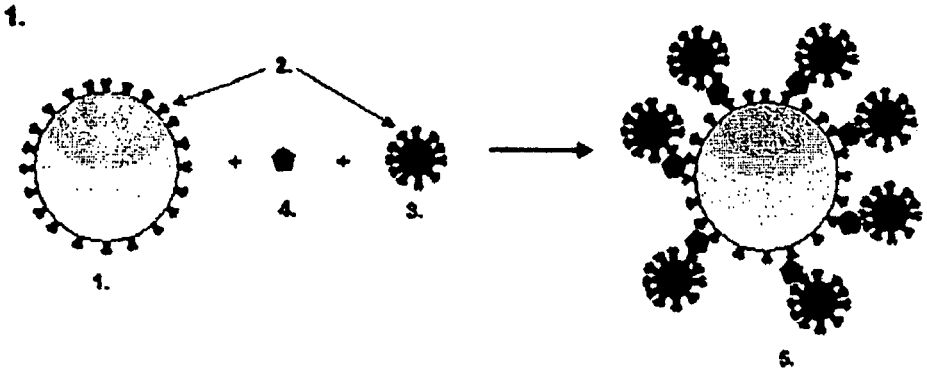
FIG. 1 discloses the assay principle for immunocomplex formation.

FIG. 1 discloses an exemplary method for immunocomplex formation. The figure describes how the first binding component together with the second binding component form said immunocomplex. Firstly, capture particles (1) coated with a binding substance (2), usually a ligand or an anti-ligand, form the first binding component. The tracer particles (3) and a binding substance (2), usually a ligand or an anti-ligand, form the second binding component. Secondly, these binding components will agglutinate when coming into contact with an analyte (4), usually a ligand or an anti-ligand, present in a sample resulting in formation of said immunocomplex (5).

Figure 2:
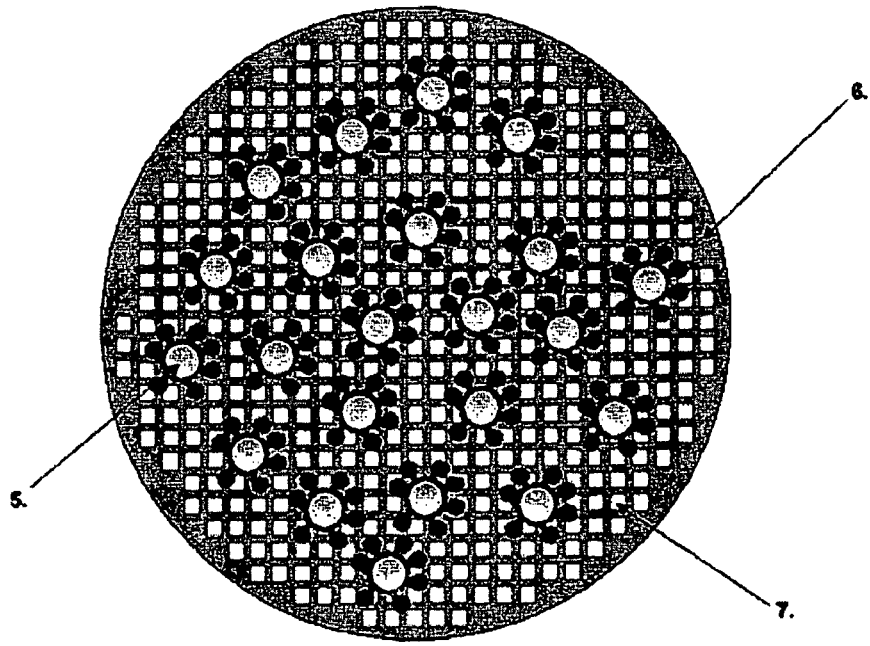
FIG. 2 discloses the two dimensional separation of said complex on the grid.

FIG. 2 shows a front view of how the two dimensional filtration occurs after applying the immunocomplexes (5) on the grid (6). Quadratic hole pattern (7) form the basic structure of the grid.

Figure 3:
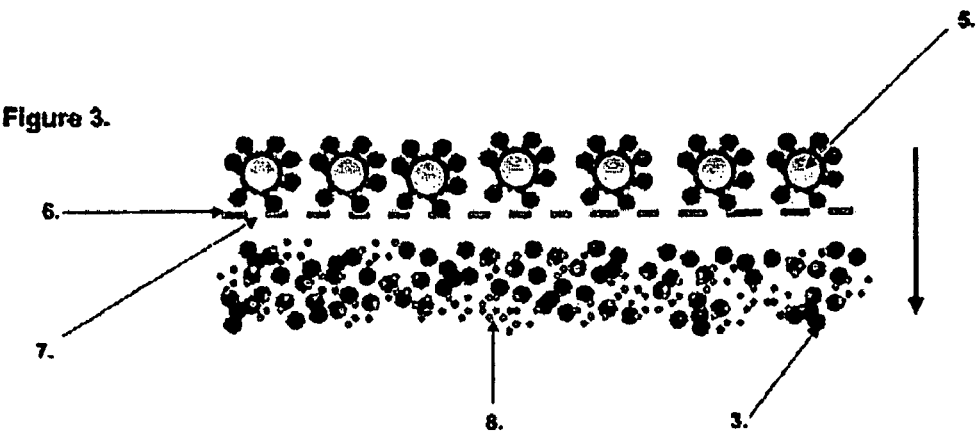
FIG. 3 discloses the three dimensional separation of unbound non-specific material by filtration of said material through the grid.

FIG. 3 shows a side view of the retained immunocomplexes (5) on the grid (6), the third dimensional filtration direction of filtrated tracer particles (3) and unwanted non-specific material (8).

Figure 4:
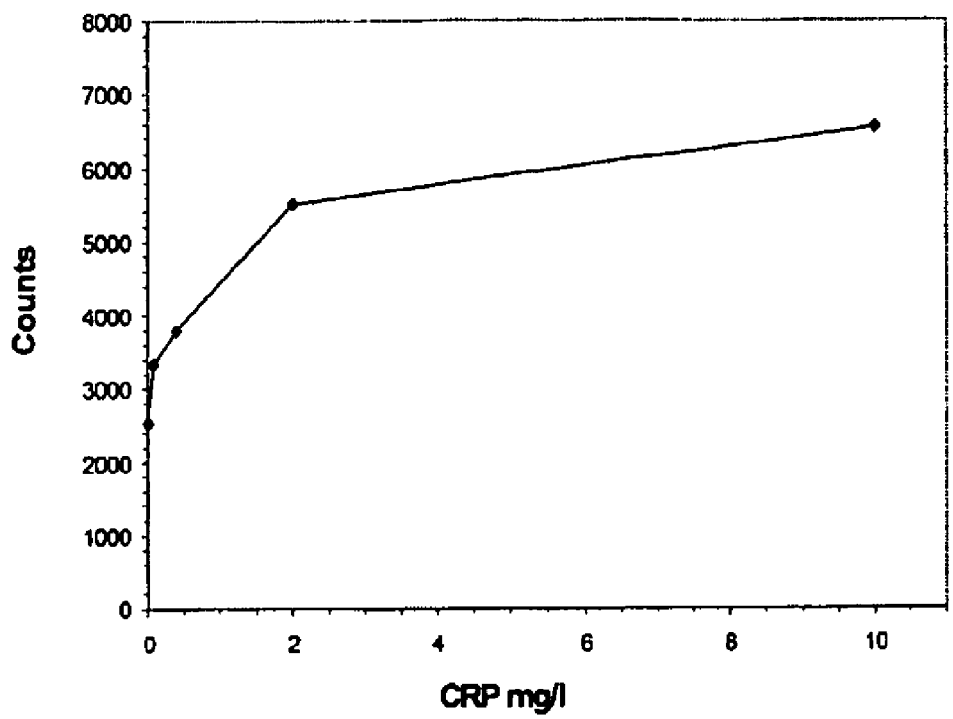
FIG. 4 describes a graph showing the concentration of hCRP in a sample.

FIG. 4 discloses a graph showing the results of an assay using hCRP as an analyte and capture and label particles coated with F(ab')$_2$ fragments of polyclonal antibodies for immunocomplex formation and separation of said complex on the grid. The assay range for hCRP is 0.08-10 mg/l.

Figure 5:
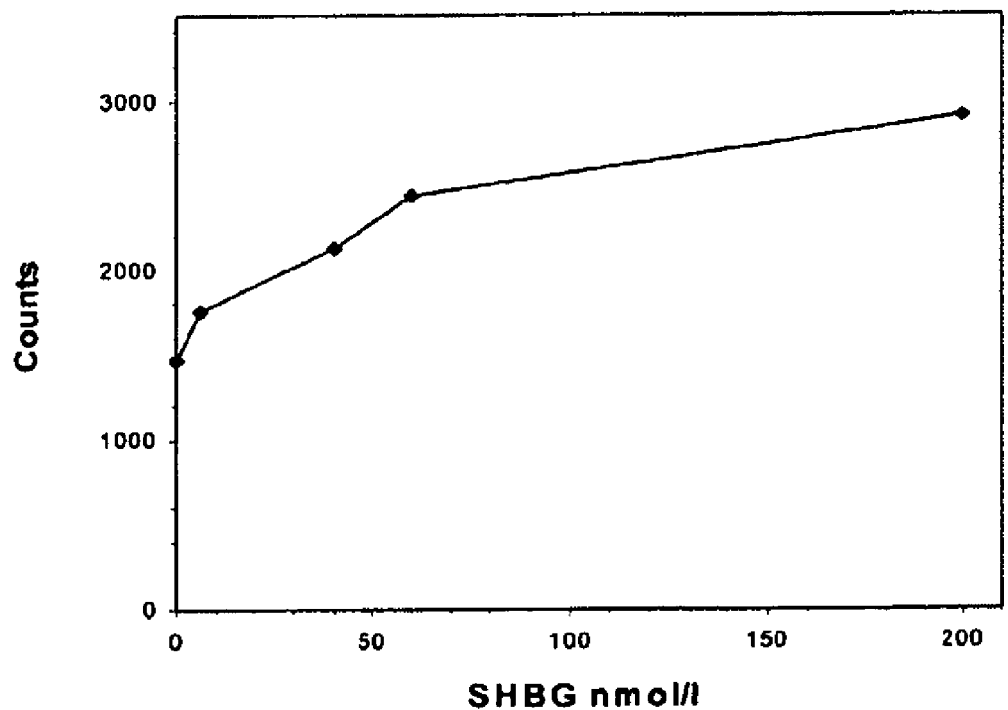
FIG. 5 describes a graph showing the concentration of hSHBG in a sample.

FIG. 5 discloses a graph showing the results of the assay using hSHBG as an analyte and capture and label particles coated with two different monoclonal antibodies for immunocomplex formation and separation of said immunocomplex on the grid. The assay range for hSHBG is 6-20 nmol/l.

FIG. 6 shows the separation of unbound second binding component from second binding component bound to a first binding component using a grill structure. Complexes containing the second and first binding components (C) cannot pass through the grill (A). Unbound second binding component (B) can pass through the grill. In an ideal case, the tangential points of the grill and the capture particles of the first binding component (D) approach to 0.

DEFINITIONS USED

The concepts used in the present invention and described herein have the following applied meanings:
  binding substance—any molecule, ligand or anti-ligand, compound, or combination thereof capable of recognising and binding to the distinct part of the specific molecule (e.g. epitope or antigenic determinant);
  ligand or anti-ligand—a molecule that forms a complex with another molecule, such as an antigen or antibody used in an immunoassay;
  first binding substance—a binding substance that is or will be coated onto capture particles;
  second binding substance—a binding substance that is or will be coated onto label particles;
  capture particle—solid particle composed of any type of polymer, plastics, glass, metal, cellulose or the like, used as a solid phase or carrier for the binding substance which, accordingly, is rendered insoluble; alternatively, different non-solid (elastic) materials like liposomes, cells, micro-organisms including viruses can function as capture particles;
  label—a substance that generates or can be made to generate a signal capable of being detected or measured by visual or instrumentation means;
  label particle—solid particle composed of any type of polymer, plastics, glass, metal, cellulose or the like, which is detectably labelled; alternatively, different non-solid (elastic) materials like liposomes, cells, microorganisms including viruses can function as label particles;

first binding component—a component comprising capture particle coated with a first binding substance;

second binding component—a component comprising label particles coated with a second binding substance;

binding components—refers to a first binding component and/or a second binding component;

first binding complex—refers to a complex between a first binding component and an analyte;

second binding complex—refers to a complex between a first binding complex (a first binding component and an analyte) and a second binding component;

third binding complex—refers to a complex between a second binding component and an analyte;

immuno- or other biomolecular complex—a first, second or third binding complex;

analyte—a compound or substance whose presence in a sample solution is to be quantitatively or qualitatively assessed and which contains at least one unique spatial or polar arrangement capable of being recognised and bound by a binding substance; the analyte can be free (separate) in solution or bound to e.g. cell membranes;

separation device—a device which encloses a porous surface mounted into said device;

porous surface—surface used for immuno- or other biomolecular complex separation from unbound material which allows the second binding component and other unbound material but not the first binding component to pass through the surface; the porous surface does not allow either the first or the second binding complex to pass through the surface; the porous surface comprises holes or openings;

holes or openings—these terms are used interchangeably herein; the holes/openings are the means by which the second binding component and other unbound material pass through the porous surface;

size of the hole/opening—this refers to the dimension of the hole/opening that limits the ability of a particle or material to pass through; the size may, for example, refer to the average diameter of a hole/opening or the distance between two parallel sides of a hole/opening;

size of the particle—this refers to the dimension of the particle that limits its ability to pass through a hole/opening; the size may, for example, refer to the average diameter of a spherical particle;

separation means or mounting—used in same meaning as porous surface;

grid, grill—specific example of porous surface having holes or openings with dimensions relative to the size of particles;

two dimensional format—material moves laterally on the porous surface because it is unable to pass through the surface; particles larger than the size of the holes/opening in the porous surface will be separated two dimensionally; the first binding component, first binding complex and second binding complex undergo two dimensional separation;

three dimensional format—material moves laterally on the porous surface and vertically through the porous surface because it is able to pass through the surface; particles smaller than the size of the holes/opening in the porous surface will be separated three dimensionally; the second binding component undergoes three dimensional separation.

DETAILED DESCRIPTION OF THE INVENTION

The present invention uses a porous surface as means of separating an immuno- or other biomolecular complex from unbound material after formation of said complex. The complex segregation occurs strictly on the surface of the porous surface (separation means).

The use of capture particles enables the use of a porous surface with holes/openings having a size which retains the first binding component, first binding complex and second binding complex on the porous surface but allows the second binding component and other unwanted material to pass through the surface. The third binding complex will either be retained on the porous surface or pass through the porous surface. Which of these options applies is dependent on the shape and size of the hole/opening.

The separation of said complexes on a porous surface from unbound material is made possible by the use of capture particles which enable the use of a porous surface with pores of larger size than if only second binding components (binding substance coated label particles) were used. The size and shape of the holes/openings of the porous surface is critical. This is discussed in more detail below. Persons skilled in the art acknowledge that particles have a tendency for autoagglutination causing false positive results. Therefore, the size of the holes should be large enough for the autoagglutinated second binding components to pass through the porous surface, allowing only a specific signal from the second binding complex indicating the presence of an analyte in the sample to be studied. Accordingly, the size of the hole should be such that autoagglutinated particles do not clog the hole. Moreover, the shape of the hole should be such that the used capture particles do not plug the hole.

The porous surface and especially the holes/openings thereof should be compatible with the size and form of the capture particle. The hole and the capture particle form a functional entirety which should be optimised to retain the binding substance coated capture particle (first binding component) on the porous surface without clogging the hole. The holes of the porous surface should, in all circumstances, maintain their ability to allow unbound second binding component and other unwanted material to pass through said surface. This is achieved by designing a functional hole-capture particle pair where the tangential contact points between the capture particle and the edge of the hole is both numerically and in respect of size of contact area as small as possible.

The present invention is especially suitable to determine low concentrations of analyte in sample. When a minor amount of analyte is attached to the binding substance exposed to a sample having a low concentration of said analyte it is not possible to determine this small amount of agglutination with conventional methods. According to the present invention it is possible to determine said analyte by exploiting the high intensity signal of the label particle. As mentioned a small amount of agglutination is insufficient to allow an accurate and reliable result, however, said agglutination can be measured by applying the method of the present invention. The present invention does not count on formed agglutination per se but relies on the label signal which intensity increases in proportion with the amount of produced agglutination. This becomes evident when a conventional immunoturbidimetric assay is compared with the present invention.

A typical agglutination test exploits particles of the size of 0.1-1.0 µm and a very accurate amount of binding substance coated thereto. The optimal concentration of binding substance coated particles enables a visible agglutination to occur. The present invention discloses a method where the concentration of binding substance used for coating either the capture or label particle can be considerably reduced. The reason why such a reduction is possible is based on the use of an intensive signal generating label which is incorporated into the label particle. As a result of the intensive signal generation a signal is achieved even when just a small amount of analyte has been captured by a reduced number of binding substance on the surface of capture particles. Accordingly, due to said intensive signal generating capacity also a small amount of binding substance coated label particles are sufficient enough for a reliable measurement.

The invention exploits a high concentration of signal generating label (not measurable in conventional low threshold response devices because of signal overflow) and a high threshold response device. The result was unexpected because the amount of label molecules used is so high that a signal overflow occurs in convention devices, whereas the amount was within measurable limits when the assay was performed according to the present invention.

Usually a small amount of label molecules can be bound to either an antibody or antigen. The present invention discloses a method where the label particles function as a carrier of numerous label molecules which results in a highly intensive signal and a greater sensitivity. The result was increased sensitivity when using devices suitable for example for point of care testing. The fluorometric assay disclosed in the present application can be performed by using a moderately sensitive low-cost device compared with a high-cost laboratory class instrument which is usually utilized when performing these types of assays without any particle enhancement. Moreover, this assay format allows numerous electro-optical designs for incorporation into low cost devices, especially for point of care type assays.

According to the present invention, there is provided a method for detecting the presence or amount of an analyte in a sample, said method comprising: (a) applying to a porous surface a first binding component comprising particles having attached thereto a binding substance that specifically binds to said analyte; (b) applying said sample to said porous surface; (c) applying to said porous surface a second binding component comprising detectably labelled particles; and (d) detecting a signal produced by said detectably labelled particles on said porous surface which is indicative of the presence and/or amount of said analyte in said sample; wherein said porous surface allows said second binding component but not said first binding component to pass through said surface; wherein said first binding component and said analyte bind to each other to form a first binding complex; wherein said detectably labelled particles have attached thereto a binding substance that specifically binds to said first binding complex, such that said second binding component and said first binding complex bind to each other to form a second binding complex; and wherein the first binding complex and/or the second binding complex is retained on the porous surface.

The assay method may be performed after completed reaction in a tube or cuvette by applying all reaction components, in one addition on the porous surface. Alternatively, the assay method can be performed by applying the first binding complex on the surface and thereafter the second binding component. Preferably all reaction components are applied in one addition.

The assay method may also be performed by first applying the sample or the first binding component on the surface followed by the second binding component. This order makes special demands on hydrophobicity and pore size of the porous surface. In such an application the sample and the second binding components should not be able to pass through the pores before completed reaction in presence of analyte in sample. Thereafter, the unbound material should have free passage through the surface generated by any means. Even further demands are put on the performance of the assay when sample or any other component small enough to pass through the holes/openings of the porous surface is applied on said surface. The escape of sample and other small components through the holes/openings can be temporarily prohibited by mechanical or physicochemical blocking.

An assay where all reactants are intermixed is more complicated because a reaction between the analyte and second binding component may result in a third binding complex. In such an assay the reaction between the analyte and second binding component occurs simultaneously with the reaction between analyte and first binding component. However, the third binding complexes retain their capacity to bind to the first binding component through the analyte.

Particles have been used as the capture surface in solid phase immunoassay of the method of the invention in order to increase the surface area for binding. By using small detectably labelled particles which are suspended in the reaction solution, favourable reaction kinetics can be achieved through increased Brownian motion. Accordingly, equilibrium can be established faster than in a system with less available surface area for binding.

When performing the immunoassay by solid phase procedures, the material will be removed from the liquid phase. When the washing is subsequently performed in the solid phase, a more complete separation is obtained and the overall sensitivity of the assay is increased.

The present invention exploits micro- or nanoparticles onto which a binding substance(s) is/are attached. The particles function on one hand as a mobile solid phase and on the other hand as a label in a heterogeneous immunoassay procedure. Especially, the particles assist in the separation of the resulting complex when using a porous surface.

The capture particles of the first binding component are preferably large (typically in micrometer size). The detectably labelled particles of the second binding component are preferably small (typically in nanometer size). However, the dimensions of the particles and the holes/openings may be reduced presuming that the size ration between the capture and label particles is maintained. The particles of the first binding component preferably have a larger average diameter than the particles of the second binding component. The separation of the resulting complex formed between said binding components and the analyte in the sample from the unbound material is carried out using a porous surface. When separated, the majority of the particle surface is on the surface of the separation means.

The capture particles can be made of any solid (e.g. plastic, glass, metal) or non-solid (i.e. elastic like liposomes, cells, micro-organism including viruses) material that can be coated with a binding substance. The label particles can also be made of any solid or non-solid material into/onto which a label or label generating material can be incorporated or attached and which can be coated with a binding substance either labelled or unlabelled. The size of the capture particles is limited by the requirements of both separation material and its properties. The binding substance coated capture particles should be large enough to be retained on the porous surface both before and after the formation of first and/or second binding complexes resulting from immuno- or chemical reaction on said porous surface. On the other hand, the size of both capture and label particles should be small enough to be suspended in solution and for increasing the binding surface.

As already mentioned, the limiting factor for the size of capture particles is the size of the opening or hole of the porous surface. The capture particles must be large enough that they do not pass through the holes/openings, while the label particles must be small enough to pass through the holes/openings. A suitable particle size ranges from an average diameter of 0.1 μm to 200 μm. The most preferred size for capture particle is an average diameter between 1-10 μm. The size of label particles is clearly smaller than that of capture particles and these label particles pass through the porous surface (e.g. grid) when not bound to capture particle-analyte (first binding) complex. The size of the label particles can vary between an average diameter of 1-1000 nm, the most preferred average diameter being between 50-150 nm. A preferable average diameter of capture particles is the micrometer size, whereas, a nanometer size is more suitable for the average diameter of the label particles.

As an example, when capture microparticles with an average diameter of 10 μm are used as in the present invention, the preferable amount of these particles varies between $4 \times 10^3$–$3 \times 10^6$ per test, the most preferred amount being $2 \times 10^4$–$2 \times 10^5$. When capture particles are used within said amount range, the preferable amount of label particles with an average diameter of 100 nm varies between $1 \times 10^8$–$2 \times 10^9$ per test.

The label particles comprising a signal or signal generating material and the second binding substance are used for increasing the specific activity of the label material. Accordingly, the use of these label particles increases the sensitivity of the assay. Luminescent, radiolabeled, magnetic or chromogenic substances can be incorporated or attached into/to particles and used as a label or signal generating material. Particles containing stabilised fluorescent labels comprising rare earth chelate have been used for labelling immunoreagents as described in U.S. Pat. No. 4,283,382, U.S. Pat. No. 4,259,313 and U.S. Pat. No. 4,735,907. These labels exhibit improved efficiency in fluorescence and are particularly useful in immunoassays. These labels also exhibit high sensitivity which accompanies their use in fluorescence spectroscopy. In addition to lanthanides such as europium, terbium, samarium, ytterbium also other luminescent, like fluorescent (e.g. fluorescein and rhodamin), phosphorescent (e.g. porphyrins), chemiluminescent (e.g. acridinium ester, luminol), electrochemiluminescent, bioluminescent, labels as well as radiolabels, chromogens such as water-insoluble or soluble dyes or magnetic labels (ferrites, magnetites), but not restricted to these, can be used in production of specific label materials in accordance with the invention.

Moreover, the invention can be extended to cover a multi-parameter assay format which exploits binding substances with different specificity coated onto the same or different capture particle(s), and labels with different characteristics.

The presence of a signal from the label particles in the second binding complex correlates to the presence of the analyte in the sample. The magnitude of signal obtained correlates to the amount of immuno/biomolecular (second binding) complex generated and thus to the quantity of analyte present in the sample. The invention preserves the use of a label also in molecular or any solid form. The level of the signal can be measured by appropriate instruments like fluorometers, luminometers, counters for radioactivity, magnetometers and spectrophotometers.

The detectably labelled particles have attached thereto a binding substance that specifically binds to the first binding complex. A binding substance "specifically binds" to the first binding complex when it binds to the first binding complex with preferential affinity compared to other complexes or substances. The binding substance may specifically bind to any part of the first binding complex. The binding substance may specifically bind to the analyte, the first binding component or both. The binding substance preferably specifically binds to the analyte.

In a particle assisted immunoreaction as disclosed in the present invention, a first binding substance is bound on the surface of the capture particle and a second binding substance is bound to particles into/to which the signal or signal generating substance has been incorporated or attached. Both the capture particle and the label particle render the binding substance insoluble. Typically, the binding substance is an antibody or fragment, for example F(ab') and F(ab')$_2$ or derivative thereof, which recognises and binds to an analyte in a sample. In the present invention both polyclonal and monoclonal antibodies may be used as binding substances. The first and second binding substances used were F(ab')$_2$-fragments of polyclonal antibodies when CRP was determined as an analyte. When SHBG was determined as an analyte two monoclonal antibodies with different specificities were used as the first and second binding substance, respectively. SHBG antibodies were represented by whole IgG molecules originating from different clones. Monoclonal antibodies as particle bound binding substances on the surfaces of both the capture particles as well as the label particles confer the high degree of specificity and sensitivity associated with such antibodies. The binding substance can be attached on the surface of the capture particles as well as on the label particles via adsorption or covalent chemical binding by using coupling methods which are well known for those skilled in the art.

It is preferred that the binding substance is bound to the particles in an amount sufficient to substantially coat the particle. By "substantially coat" is meant that some but not all of the surface area of the particles is coated. This retains spatial movement of the binding substance. The minimum percentage of the surface area of the particles coated depends partly on the type and intensity of the label used. The more intense the label the less binding substance is needed on capture particles. The assays of the present application concerning particles coated by differing amounts of binding substance were performed by using low threshold response device.

The separation assays of the present application were performed by using a high threshold response device for time resolved fluorescence measurement. When using a less sensitive simple device label particles had to be used at the concentration of about 100 times higher as compared to the amount of particles when using more sophisticated low threshold response device. The behaviour of the coated particles (concerning both capture and label particles) is not (fundamentally) different when the amount of label particles in reaction is increased for example by 100-fold.

As already mentioned above, the present invention concerns the use of a porous surface as a separation means for separating an immuno/biomolecular complex from unbound material after an immuno- or chemical reaction has occurred. The immuno/biomolecular complex segregation occurs strictly on the surface of the porous surface (separation means).

The principle of the assay, as disclosed in the present invention, relies on the separation of capture particles and label particles on a porous surface. This separation is generally dependent upon the shape and size of the particles and the holes/opening in the porous surface.

The holes/openings may be any shape, for example, square, rectangular, circular, triangular, hexagonal or octagonal. The hole/opening preferably has two parallel sides. The holes/openings may be formed by connection of the two parallel sides by two ends each formed from one straight side of any length. These ends may be at right angles to the parallel sides, for example the hole/opening is a square or a rectangle, or the ends may be at other angles, for example the hole/opening is a parallelogram or a rhombus. Alternatively, the holes/openings may be formed by connection of the two parallel sides by two ends each comprising more than one straight sides of any length. The straight sides of these ends may comprise two (for example the hole/opening is a hexagon), three (for example the hole/opening is a octagon), four (for example the hole/opening is a decagon) or more straight sides.

The multiple straight sides forming these ends may be the same or different lengths. The hole/opening may therefore be a regular or irregular shape. The ends may be at right angles to the parallel sides, for example the hole/opening is a square or a rectangle, or the ends may be at other angles, for example the hole/opening is a parallelogram or a rhombus. The two parallel sides may be connected by two or more sides of any length. Alternatively, the holes/openings may be formed by connection of the two parallel sides by two ends each comprising sides that form part of a circle, for example a semi-circle. Alternatively, the holes/openings may be formed by connection of the two parallel sides by two ends each comprising irregular sides of any shape.

In one embodiment, the holes/openings with parallel sides extend almost entirely across the porous surface, for example the porous surface is a grill. In another embodiment, the holes/openings cover almost all of the surface, for example the porous surfaces is grid. Such embodiments are most efficient for passage of unbound material through the surface because there are increased passages through which the material may travel.

The size of the capture particle is generally larger than the openings/holes of the porous surface. Moreover, the holes/openings of said surface are generally larger than the size of the label particles used in any form in the assay. In one embodiment, the porous surface comprises openings/holes with two parallel sides and the distance between these sides is smaller than the size of the capture particles of the first binding component but larger than the size of the label particles of the second binding component.

The preferred shape of the capture particle, compatible with the shape of the hole, is spherical when the shape of the hole/opening has two parallel sides as discussed above. The average diameter of the spherical capture particle is preferably larger than the distance between the two parallel sides. Similarly, the preferred shape of the label particle, compatible with the shape of the hole, is spherical when the shape of the hole/opening has two parallel sides as discussed above. The average diameter of the label particle is preferably smaller than the distance between the two parallel sides.

If a rod shaped capture particle is used then the width of said particle should always exceed the size (for example, the average diameter or distance between two parallel sides) of the hole/opening. If a rod shaped label particle is used then the width of said particle should always be less than the size (for example, the average diameter or distance between two parallel sides) of the hole/opening.

A preferable size for a surface opening or hole/opening is at least twice the size of a label particle. It is important that the surface hole/opening size is related to the size of the capture particles so as to prevent the capture particles from passing through the porous surface (e.g. grid). The typical average hole/opening size (for example, the average diameter or distance between two parallel sides) is between 0.05-100 µm, more preferably between 1-20 µm. The size of the holes/openings (for example, the average diameter or distance between two parallel sides) should be 10-90%, preferably 50-70% of the diameter of the capture particle. The size of the label particle should be in maximum 50% of, preferably 0.1-10% of the size (for example, the average diameter or distance between two parallel sides) of the hole. For example for a maximum capture particles size of 200 µm, the maximum size of the hole/opening is 180 µm.

The majority of the first binding component protrudes above the porous surface and only a minor part aligns tangentially in the holes of the porous surface. As a result, the second binding component is able to freely move through the surface by either passive or active means.

Only the label bound to capture particles in the second binding complex is measured in this assay. The immuno- or chemical reaction which assists the binding of label particle to capture particles can take place in a tube, cuvette or alike or on the porous surface.

The structure of the surface and the material used do not enable any binding inside the surface. All first binding components and second binding components attached thereto are retained upon the surface, whereas, all unbound label material flows through the surface. All material separated can either be retained on or released from surface for quantitative analyses of label. Usually the surface has a passive nature in collecting complexes, either immuno- or biomolecular complexes. However, a porous surface (e.g. grid) can also have an active role in signal generation and/or conduction as well as in removing of unbound label. Suitable means for signal generation is for example luminescence, electromagnetic radiation and magnetometry. Moreover, it is possible to allow the porous surface material to reflect or conduct the signal from second binding component bound to first binding component by electric, electromagnetic or magnetic means. The nature of the porous surface material to be chosen should expose a low background and a high signal to noise ratio. Preferred materials which fulfill the above requirements include, but are not limited to metals, silicon compounds and low background polymers. With the term "low background polymer" is meant any polymer material with very low (unspecific) signal ratio compared with the signal generated by the (specific) label. The low background polymer is a polymer which does not interfere with the label (signal) measurement. On the other hand materials, also having low background, but which actively takes part in the measurement by participating in the initiation of the specific signal can be used. Such materials includes, but are not limited to materials preferably used in fluorometric membrane-bottom microtiter plates, for example Acrowell GHP (Pall-Gelman Laboratory) or Multi-screen-FL, polycarbonate (Millipore).

Suitable porous materials are well known for those skilled in the art. For example, it is preferred that the porous surface acts as light guide in light excitation and emission applications. Moreover, electrical conductivity and semiconductor properties are preferred in electric signal generation and collection, whereas, magnetometric properties are appropriate for magnetometric assays.

The porous surface is preferably a grid. A suitable grid is for example the one used in electron microscopy as the sample support (holder). Said microscopic grids can be prepared for example from metals like copper, nickel, aluminium, molybdenum, titanium, silver and/or gold. In addition to these metals they can also be prepared from ceramics, glass or from more flexible materials like different kind of plastics and/or silicon.

The structure of the grid can be expressed in the form of a simple planar plane, wall of a tube or walls of a closed space, for example a gate. Consequently, it is possible to design and manufacture various constructions where different grid structures are present. Modem micromachining technics as micro-injection molding, hot embossing or silicon micromachining enable realisation of very complicated grids. Grids manufactured and finalised by those modern procedures may be applied in grid structures in modern analytical diagnostic devices according to the disclosure of the present invention.

The separation of the immunocomplex may be preceded by a washing step after first immunoreaction between analyte and the first binding component. The washing step may be carried out in, for example, tubes prior to applying the complex to the surface. The washing step may include the addition of a buffer. Centrifuging and resuspending of the pelleted particles removes unbound sample material as well as the free unbound analyte especially when testing high analyte concentrations. After the second immunoreaction between the first binding component-analyte complex and the second binding component the reaction components may be transferred onto the porous surface (e.g. grid). Alternatively, depending on the structure of the separation means, both immunoreactions can also be carried out directly on the porous surface (e.g. grid). The washing may also be accomplished by adding the buffer solution onto the porous surface (e.g. grid). The washing solution (or buffer) is preferably capable of passing through the porous surface. The buffer flushes the complex, porous surface (e.g. grid) and its holes and removes unbound label particles thus decreasing background signal. Because the efficiency of the assay technique is partly dependent on completeness of separation between bound and unbound material, the washing step is more effective when more wash fluid is in contact with the binding components. The completeness of the wash decreases the background signal present, where unbound signal generating material remains in area of measurement. The advantages of using a metallic grid as the porous surface is that the material intrinsically has very low background fluorescence and the unspecific binding of label particles as well as sample constituents onto the grid is small.

The present invention comprises a generic method of achieving an unique separation method. Said separation method consists in practice of both a two and a three dimensional separation. Material such as first binding component and first and second binding complexes which do not pass through the openings (holes) of the porous surface (e.g. grid) because of their larger size moves in a planar plane e.g. is separated two dimensionally. Other material such as excess second binding component, unwanted material which may cause unspecific binding and being small enough to pass through the openings exploits a three dimensional route. This allows a pure immuno/biomolecular (first and second binding) complex to be established on the porous surface.

Accordingly, the separation of bound immuno/biomolecular complex from unbound material is achieved by using said surface where the separation occurs mainly two dimensionally on the surface. Interestingly, the disclosed surface enables a separation where said complexes are distributed two dimensionally on the surface, whereas unbound materials are distributed three dimensionally. Accordingly, said method enables both a two and a three dimensional separation. This feature very clearly distinguish the present invention from that of known prior art. Said feature enables, when needed, the release and transfer of complexes from the surface of the porous surface (e.g. grid). Another important advantage of this separation method is that no additional means, for example a magnet which is employed when magnetic beads are used, are needed for separation. According to the present invention the separation occurs on a surface i.e. on the test or assay mounting, which as such already is considered to be a basic tool to perform an assay. The advantage of using said surface for immuno/biomolecular complex separation is the low unspecific label binding and thus the high signal to noise ratio. It is also advantageous to select a surface material which do not bind non-specifically label or label particles.

Furthermore, the three dimensional separation using a porous surface can be made faster and more efficient by applying the porous surface on the surface of a wicking member, matrix or any other kind of membrane or filter. The purpose being to enable the flow of fluids containing unbound material through the porous surface (e.g. grid). Material comprising a gel layer underneath the porous surface for collecting the unbound material can also be used to improve the features of the porous surface.

Assay which exploit a classical three dimensional membrane rely on separation of bound from unbound material, where some of the bound material is bound inside the membrane and some on the surface of the membrane. The present invention relies on a separation of bound and unbound material, where, the bound material is bound on the porous surface. In practice, this means that the majority of the first binding components extends above the porous surface and only a minor part, if any, is in openings or the holes of the porous surface. Said distribution is highly dependent on the diameter of the holes and the size of the particles. The particles can be applied on the porous surface (e.g. grid) as a mono- bi-, or multilayer in the method of the invention.

Typically the assay method used is a non-competitive assay. The assay method used may also apply on a competitive assay procedure. In a non-competitive assay the intensity of the signal, whereas in a competitive assay the decrease of signal intensity is measured.

According to the method of the present invention all immunoreactions can be carried out either sequentially or simultaneously in a tube or cuvette or directly on the surface of the grid. Typically, the total incubation (assay) time is 1 to 5 minutes when all immunoreactions are carried out simultaneously and 3 to 15 minutes, respectively, when immunoreactions are carried out sequentially. The assay method may however take less or more time than this. The method is particularly suitable for analytes which have more than one specific binding sites.

The method of the invention is generally applied to a sample, typically a biological sample in the field of infectious diseases, clinical chemistry and hygiene monitoring. Typically the sample is one which is known or suspected of being a body sample from an individual, such as a human. Preferably the sample comprises a body fluid e.g. blood, serum, plasma, cerebrospinal fluid, urine, saliva, healing wound fluid, ascitic fluid, pleural fluid, synovial fluid, suction blister fluid of skin or amniotic fluid. Moreover, the method is also suitable for testing water soluble solid or semisolid or pasty samples such as faeces, sputum, pharyngeal, pus and alike. Furthermore, the method can be exploited in hygiene monitoring in food and other industry, as well as hospitals, laboratories etc.

The method described can be used for the separation of immunocomplexes and thus for the detection of micro-organisms as bacteria, viruses, fungi and parasites (protozoas) and their antigens as well as eukaryotic cells and their antigens. Additionally, the following kinds of analytes can be determined: hormones, drugs, toxins, vitamins, environmental chemicals, enzymes, peptides, proteins, glycoproteins, lipoproteins, lipids, haptens, allergens, and nucleic acids. The method described can also be used for the separation and analysis of other types of biomolecular complexes like e.g. complexes between nucleic acids (DNA-DNA and DNA-RNA) and between nucleic acids and proteins (e.g. regulatory complexes controlling gene expression). Said biomolecular complexes comprise also other types of complexes between different proteins (including glyco- and lipoproteins) as complexes between ligand and receptor (receptor bound to whole cell membranes or to separated cellular membranes), multi-enzyme complexes (comprising different enzyme subunits) as well as complexes between proteins and other types of biomolecules as complexes between enzyme and its substrate. The analyte may be cellular antigen free (e.g. nucleic acid or cytoplasmic protein) or bound to prokaryotic or eukaryotic cell membrane (e.g. receptors).

The invention also provides a kit for detecting the presence and/or amount of an analyte in a sample. In addition to a porous surface and first and second binding components, the kits of the invention may comprise a suitable buffer, a suitable calibration reagent, a wicking membrane, a sampling device, instructions for use and other common components.

EXAMPLES

The following Examples illustrate the invention. Unless indicated otherwise, the methods used are standard biochemistry and molecular biology techniques. The Examples presented are examples only and not intended to limit the scope of the invention.

The material of the metallic grids used in the present invention for immunocomplex separation and assay mounting was copper. The thickness of the grids used were approximately 10 μm with a bar thickness of 5 μm and showed a hole size of 7.5 μm (2000 mesh). The grid used in the present invention are similar to those used in electron microscopy as the sample support (holder).

Example 1

Procedure for sequential assay of hCRP with first and second particle bound binding substance exploiting polyclonal F(ab')$_2$-fragments and measuring immunocomplex formation on the grid used for separation of said complex (FIG. 4).

Human C-reactive protein (hCRP) assays are used as an indicator of inflammation. In the present example hCRP was determined in a calibrator sample. First, a sample containing hCRP at a concentration between 0-10 mg/l and 0.1 ml of the buffer (Tris based) are added to small centrifugal tubes. Thereafter, 10 μl of 0.25% latex particles (diameter 10 μm) coated with anti-CRP F(ab')$_2$ fragment are added and the tubes are incubated for 5 min with mixing. After incubation the tubes are centrifuged for 0.5-3 min (about 16000×g) and the supernatants are discarded. Latex particles with bound CRP are then washed to remove unbound CRP by means of centrifugation and aspiration. The particles are resuspended to 0.1 ml of buffer and 10 μl of label containing binding substance coated latex particles (0.125% suspension; latex particle diameter 0.1 μm) are added. After 5 min incubation the formed immunocomplex: capture latex with first binding substance—CRP—label latex with the second binding substance is separated by transferring the reaction components on 7.5 μm (hole diameter) grids and filtrated through said grids (diameter 3 mm). The filtration process is described in FIGS. 2 and 3. After washing the fluorescence signal of the grid bound immunocomplex is counted. The signal correlates to the amount of immunocomplex on the grid and thus to amount of CRP in said complex and, consequently, to the amount of analyte in the sample.

Example 2

Procedure for sequential assay of hSHBG with first and second particle bound binding substance exploiting monoclonal antibodies and measuring immunocomplex formation on the grid used for separation of said complex (FIG. 5).

Human sex hormone binding globulin (hSHBG) assays are used as one indicator for hormone status. In the present example recombinant hSHBG was determined in a sample of cell culture medium. First, a sample containing hSHBG at a concentration between 0-200 nmol/l and 0.1 ml of the buffer are added to small centrifugal tubes. Thereafter, 10 μl of 0.25% latex particles (diameter 10 μm) coated with monoclonal anti-SHBG antibody are added and the tubes incubated for 5 min with mixing. After incubation the tubes are centrifuged for 0.5-3 min (about 16000×g) and the supernatants are discarded. Latex particles with bound SHBG are then washed to remove unbound SHBG by means of centrifugation and aspiration. The particles are resuspended to 0.1 ml of buffer and 10 μl of label containing binding substance coated latex particles (0.125% suspension; latex particle diameter 0.1 μm) are added. The binding substance being a monoclonal antibody with different specificity for SHBG than the first binding substance. After 5 min incubation the formed immunocomplex: capture latex with first binding substance—SHBG—label latex with the second binding substance is separated by transferring the reaction components on 7.5 μm (hole diameter) grids and filtrated through said grids (diameter 3 mm). The filtration process is described in FIGS. 2 and 3. After washing the fluorescence signal of the grid bound immunocomplex is counted. The signal correlates to the amount of immunocomplex on the grids and thus to amount of SHBG in said complex and, consequently, to the amount of analyte in the sample.

The invention claimed is:

1. A method for detecting the presence or amount of an analyte in a sample, said method comprising:
    (a) applying to a porous surface a first binding component comprising particles having attached thereto a binding substance that specifically binds to said analyte;
    (b) applying said sample to said porous surface;
    (c) applying to said porous surface a second binding component comprising detectably labelled particles; and
    (d) detecting a signal produced by said detectably labelled particles on said porous surface which is indicative of the presence and/or amount of said analyte in said sample;
    wherein said porous surface comprises one or more holes or openings;
    wherein said holes or openings allow unbound second binding component but not said first binding component to pass through said surface;
    wherein said first binding component and said analyte bind to each other to form a first binding complex;
    wherein said detectably labelled particles have attached thereto a binding substance that specifically binds to said first binding complex, such that said second binding component and said first binding complex bind to each other to form a second binding complex;
    wherein the first binding complex and second binding complex are retained on the porous surface; and
    wherein contact between the particles of the first binding component with holes or openings of the porous surface does not prevent second binding component that is not present in a second binding complex from passing through the same holes or openings.

2. The method according to claim 1, wherein the sample and first binding component are contacted with one another before being applied to the surface.

3. The method according to claim 1, wherein step (a) is carried out before step (b).

4. The method according to claim 1, wherein the sample, first binding component and second binding component are contacted with one another before being applied to the porous surface.

5. The method according to claim 1, further comprising applying to said surface before step (d) a washing solution capable of passing through said porous surface.

6. The method according to claim 1, wherein said second binding component comprises detectably labelled particles having attached thereto a binding substance that specifically binds to said analyte.

7. The method according to claim 1, wherein said porous surface comprises a material which is metal, plastic, ceramic, glass or silicon.

8. The method according to claim 1, wherein said porous surface is a separation device.

9. The method according to claim 8, wherein said separation device comprises a two and/or three dimensional separation.

10. The method according to claim 1, wherein said porous surface is a grid.

11. The method according to claim 1, wherein the particles of the first binding component or the second binding component:
   (a) comprise a material which is synthetic polymer, plastic, glass, metal or cellulose; or
   (b) are liposomes, cells or micro-organisms.

12. The method according to claim 1, wherein the particles of the first binding component have an average diameter of from 0.1 to 200 μm.

13. The method according to claim 1, wherein the particles of the second binding component have an average diameter of from 1 to 1000 nm.

14. The method according to claim 1, wherein said holes or openings have two parallel sides and the distance between the parallel sides is smaller than the average diameter of the particles of the first binding component.

15. The method according to claim 1, wherein said binding substance is adsorptively or covalently bound to said particles in an amount sufficient to substantially coat the particles.

16. The method according to claim 1, wherein said binding substance comprises a monoclonal antibody, a polyclonal antibody or F(ab') or F(ab')$_2$ fragments thereof.

17. The method according to claim 1, wherein said particles are detectably labelled using a material which is a luminescent, radiolabeled, chromogenic or magnetic material.

18. The method according to claim 1, wherein said analyte is an antigen.

19. The method according to claim 18, wherein the antigen is C-reactive protein (CRP) or sex hormone binding globulin (SHBG).

20. A kit for detecting the presence and/or amount of an analyte in a sample comprising:
   (a) a porous surface comprising one or more holes or openings;
   (b) a first binding component comprising particles having attached thereto a binding substance that specifically binds to said analyte to form a first binding complex; and
   (c) a second binding component comprising detectably labelled particles which have attached thereto a binding substance that specifically binds to said first binding complex, such that said second binding component and said first binding complex bind to each other to form a second binding complex; wherein the first binding complex and the second binding complex are capable of being retained on the porous surface; second binding component that is not present in a second binding complex, but not said first binding component, can pass through said porous surface; and contact between the particles of the first binding component with the holes or openings of the porous surface does not prevent second binding component that is not present in a second binding complex from passing through the same holes or openings.

21. The method of claim 1, wherein said porous surface is a metal grid or grill.

22. The kit of claim 20, wherein said porous surface has a passive nature in collecting said complexes and optionally has an active role in signal generation and/or conduction as well as in removing unbound label.

23. The method of claim 1, wherein said porous surface has a passive nature in collecting said complexes and optionally has an active role in signal generation and/or conduction as well as in removing unbound label.

* * * * *

UNITED STATES PATENT AND TRADEMARK OFFICE
CERTIFICATE OF CORRECTION

PATENT NO. : 7,709,212 B2  Page 1 of 1
APPLICATION NO. : 11/720701
DATED : May 4, 2010
INVENTOR(S) : Luotola et al.

It is certified that error appears in the above-identified patent and that said Letters Patent is hereby corrected as shown below:

Column 4,
    Line 48, replace "immunoibiomolecular" with --immuno/biomolecular--.

Column 6,
    Line 29, replace "6-20 nmol/l" with --6-200 nmol/1--.

Column 15,
    Line 5, replace "Modem" with --Modern--.

Signed and Sealed this

Twenty-sixth Day of October, 2010

David J. Kappos
*Director of the United States Patent and Trademark Office*